United States Patent [19]

Licciardello et al.

[11] 4,435,331

[45] Mar. 6, 1984

[54] METHYL CARBONATE OF α,3,3-TRIMETHYL CYCLOHEXANE METHANOL, ORGANOLEPTIC USES THEREOF AND PROCESS FOR PREPARING SAME

[75] Inventors: Michael Licciardello, Little Silver; Richard M. Boden, Ocean, both of N.J.

[73] Assignee: International Flavors & Fragrances Inc., New York, N.Y.

[21] Appl. No.: 474,158

[22] Filed: Mar. 10, 1983

[51] Int. Cl.[3] .............................................. C07C 69/96

[52] U.S. Cl. ..................................... 260/463; 252/8.6; 252/8.9; 252/174.11; 252/522 R

[58] Field of Search .......................................... 260/463

[56] References Cited

U.S. PATENT DOCUMENTS

| | | | |
|---|---|---|---|
| 3,847,975 | 11/1974 | Hall | 252/522 |
| 3,959,508 | 5/1976 | Pittet et al. | 426/534 |
| 4,028,279 | 6/1977 | Van Onwerkerr et al. | 252/522 |
| 4,033,993 | 7/1977 | Bruns et al. | 260/463 |
| 4,181,676 | 1/1980 | Buysch et al. | 260/463 |
| 4,217,253 | 8/1980 | Schmitt | 252/522 R |

*Primary Examiner*—Mary C. Lee
*Assistant Examiner*—Chabi C. Kalita
*Attorney, Agent, or Firm*—Arthur L. Liberman

[57] ABSTRACT

Described is the methyl carbonate of α,3,3-trimethyl cyclohexane methanol defined according to the structure:

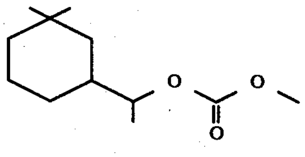

and uses thereof in augmenting or enhancing the aroma of perfume compositions, colognes and perfumed articles such as solid or liquid anionic, cationic, nonionic or zwitterionic detergents, fabric softeners, fabric softener articles as well as hair sprays, shampoos and bath oils and perfumed polymers. Also described is a process for preparing the methyl carbonate of α,3,3-trimethyl cyclohexane methanol according to the reaction:

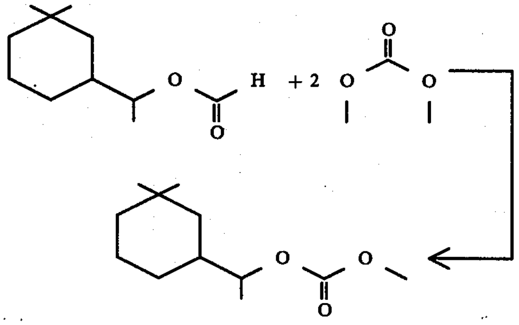

1 Claim, 3 Drawing Figures

GLC PROFILE FOR EXAMPLE I.

GLC PROFILE FOR FRACTION 5 OF EXAMPLE I.

NMR SPECTRUM FOR EXAMPLE I.

METHYL CARBONATE OF α,3,3-TRIMETHYL CYCLOHEXANE METHANOL, ORGANOLEPTIC USES THEREOF AND PROCESS FOR PREPARING SAME

BACKGROUND OF THE INVENTION

The instant invention relates to the novel methyl carbonate of α,3,3-trimethyl cyclohexane methanol defined according to the structure:

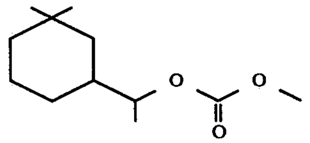

and uses thereof in augmenting or enhancing the aroma of consumable materials.

Materials which can provide woody, floral (carnation), animalic (castoreum), spicy (cardamon), ylang, cananga and caryophyllene-like aroma nuances are well known in the art of perfumery. Many of the natural substances which provide such fragrances and contribute the desired nuances to perfumery compositions are high in cost, vary in quality from one batch to another and/or are generally subject to the usual variations of natural products.

The prior art contains a large number of teachings regarding the use of organic carbonates in augmenting or enhancing the aroma of perfumes. Thus, U.S. Pat. No. 4,033,993 discloses the use of organic carbonates defined according to the structure:

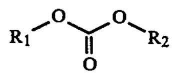

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynyl having from 2 to 5 carbon atoms. U.S. Pat. No. 4,033,993 describes, for example, methyl-1-ethynycyclohexyl carbonate having a fruity, herbal complex odor and distinct fragrance of dill. In addition, U.S. Pat. No. 4,033,993 describes methyl cyclooctyl carbonate as having an herbal, natural and complex fragrance which is distinguished by a strong and long clinging flowery jasmine scent and further indicates its use in jasmine perfume compositions. U.S. Pat. No. 4,033,993 describes the preparation of the compounds defined according to the structure:

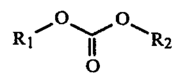

according to the reaction:

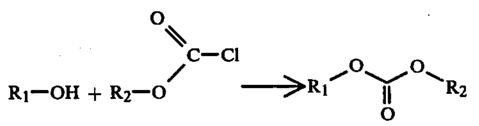

where $R_1$ and $R_2$ are defined as above.

In addition, U.S. Pat. No. 4,080,309 describes the perfume use of the carbonates defined according to the structure:

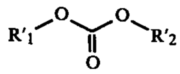

wherein $R_1'$ is a moiety having from 8 to 12 carbon atoms selected from the group consisting of alkylcyclohexyl, alkenylcyclohexyl, alkynylcyclohexyl and cycloalkyl and $R_2'$ is a moiety selected from the group consisting of alkyl having from 1 to 5 carbon atoms, alkenyl having from 2 to 5 carbon atoms and alkynyl having from 2 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of 4,080,309 are indicated to be prepared according to the reaction:

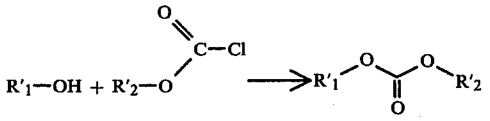

Nothing in the prior art, however, discloses the methyl carbonate of α,3,3-trimethyl cyclohexane methanol of our invention having the specific fragrance nuances as set forth above.

The corresponding formate defined according to the structure:

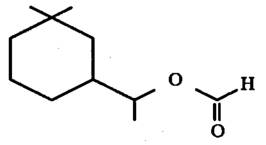

has a known use in perfumery as set forth in U.S. Pat. No. 3,847,975 issued on Nov. 12, 1974 the specification for which is incorporated by reference herein.

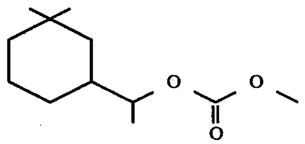

Figure 2:
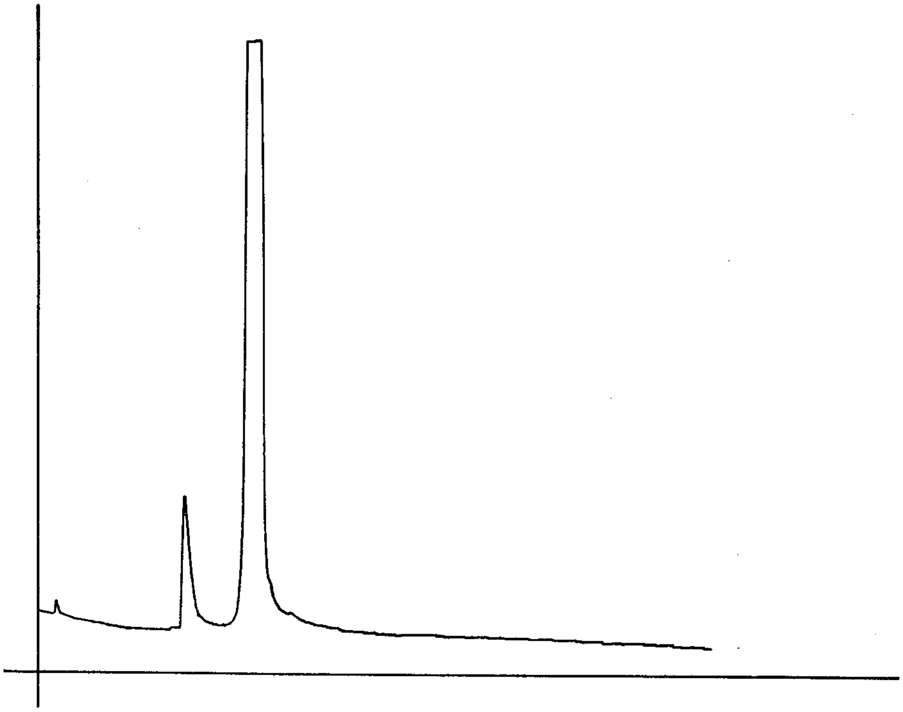

FIG. 2 is the GLC profile for Fraction 5 of the distillation product of the reaction product of Example I containing the compound having the structure:

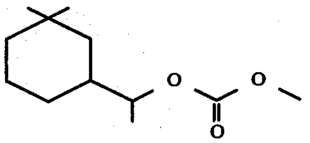

Figure 3:
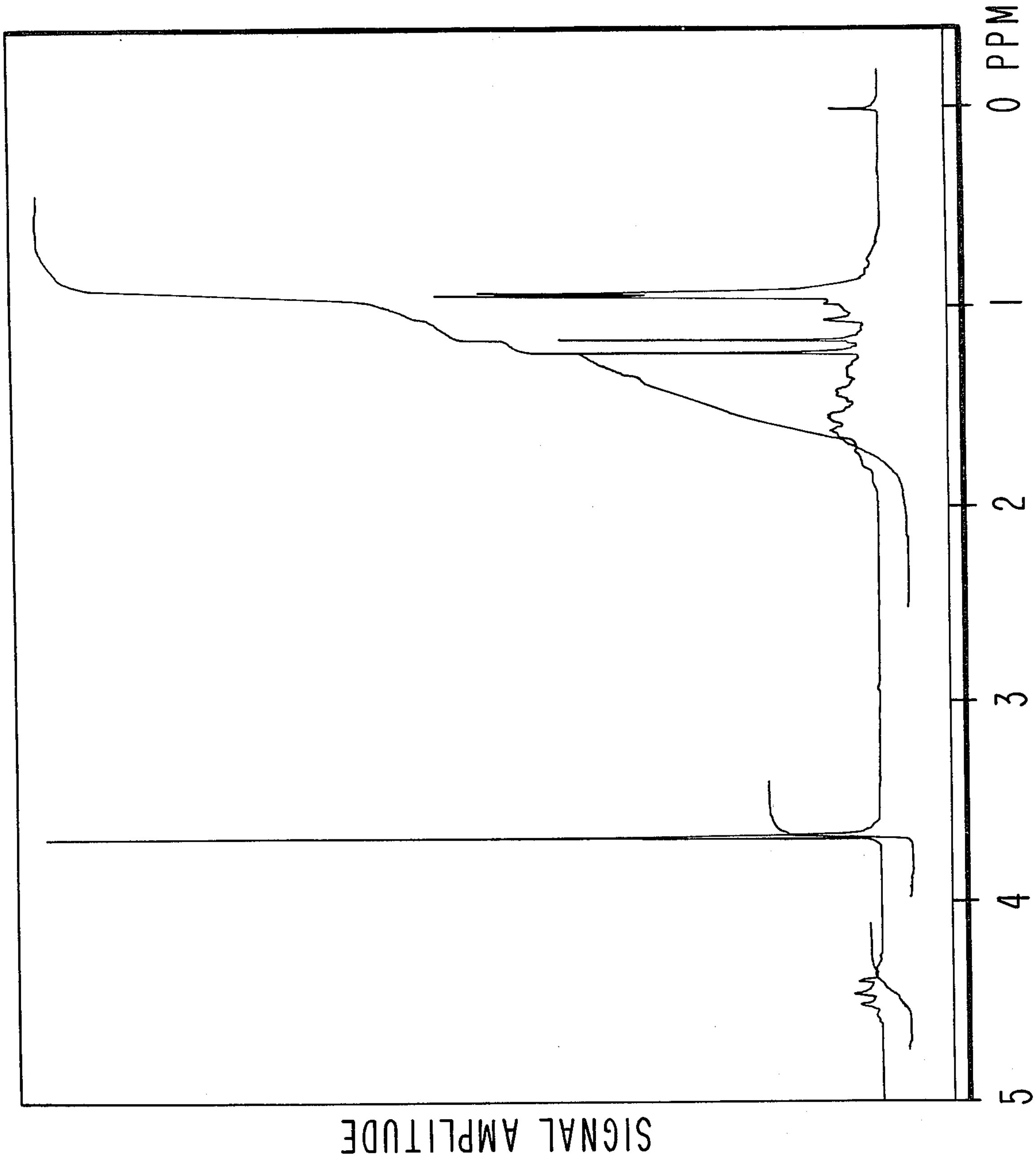

FIG. 3 is the NMR spectrum for the compound having the structure:

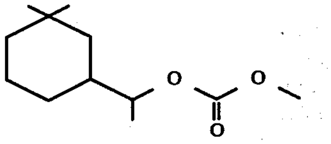

produced according to Example I. (Conditions: Field strength 100 MHz; solvent: $CFCl_3$).

THE INVENTION

The present invention provides the compound, methyl carbonate of α,3,3-trimethyl cyclohexane methanol having the structure:

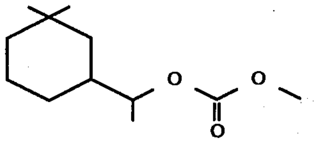

The present invention also provides an economical efficient process for synthesizing the compound methyl carbonate of α,3,3-trimethyl cyclohexane methanol having the structure:

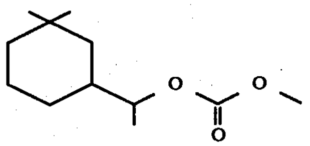

by reacting dimethyl carbonate with α,3,3-trimethyl cyclohexyl formate having the structure:

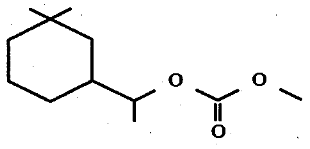

in the presence of an alkali metal alkoxide according to the reaction:

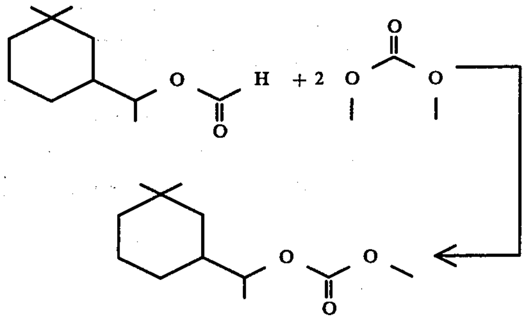

the formula of the alkali metal alkoxide being MOR" wherein R" represents lower alkyl such as methylethyl, propyl, n-butyl and tertiary butyl and M represents alkali metal such as sodium potassium and lithium.

The present invention also provides processes for using the methyl carbonate of α,3,3-trimethyl cyclohexane methanol having the structure:

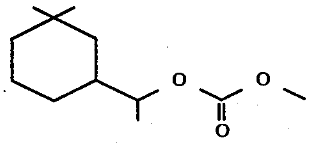

for its organoleptic properties in augmenting or enhancing the organoleptic properties of consumable materials, that is, the aroma of perfumes, colognes and perfumed articles (such as perfumed polymers, solid or liquid cationic, anionic, nonionic or zwitterionic detergents, soaps, fabric softener compositions, drier-added fabric softener articles such as BOUNCE® registered trademark of the Procter & Gamble Company of Cincinnati, Ohio, fabric brighteners, cosmetic powders, bath preparations, hair preparations such as hair sprays and shampoos).

The methyl carbonate of α,3,3-trimethyl cyclohexane methanol of our invention may be prepared by first reacting the α,3,3-trimethyl cyclohexyl methyl formate having the structure:

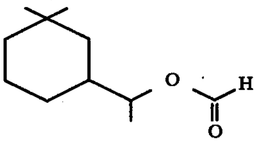

with dimethyl carbonate according to the reaction:

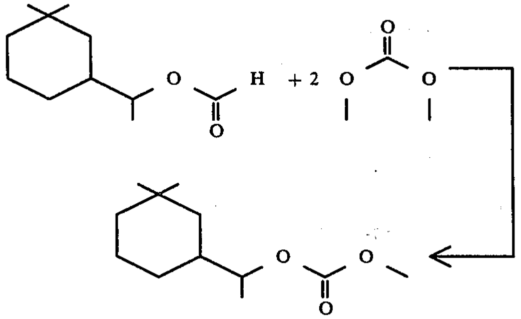

in the presence of an alkali metal alkoxide such as sodium methoxide, sodium ethoxide, sodium-t-butoxide, potassium methoxide, potassium ethoxide and potassium-t-butoxide. The reaction between the formate ester and the dimethyl carbonate takes place in the absence of any additional solvent. The mole ratio range of dimethyl carbonate:formate ester may vary from 3 moles dimethyl carbonate:0.5 moles formate ester down to 1 mole dimethyl carbonate:1 mole formate ester. It is preferred that the mole ratio of dimethyl carbonate:formate ester be about 2:1. The molar concentration in the reaction mass of the alkali metal alkoxide catalyst may vary from about 0.005 up to about 0.01 with a mole ratio of about 0.05 being preferred.

The reaction temperature range may vary from about 50° C. up to about 100° C. and the reaction pressure may vary from atmospheric pressure up to about 10 atmospheres. Higher temperature of reaction necessitates higher pressure over the reaction mass in order to prevent the reaction product from evaporating therefrom.

At the end of the reaction, the reaction product is purified according to standard procedures such as fractional distillation and, if necessary, chromatographic separation as by high pressure liquid chromatography or GLC (vapor phase chromatography).

The methyl carbonate of α,3,3-trimethyl cyclohexane methanol of our invention having the structure:

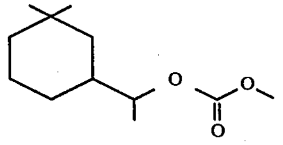

can be used to contribute woody, floral (carnation), animalic (castoreum), spicy (cardamon), ylang, cananga and caryophyllene-like aroma nuances to perfume compositions, perfumed articles such as solid or liquid cationic, anionic, nonionic or zwitterionic detergents, perfumed polymers, (e.g., perfume polyethylene, perfume propylene and perfume poly(epsilon caprolactone), fabric softener compositions, fabric softener articles, optical brighteners, fabric conditioners, hair preparations, shampoos and hair sprays. As olfactory agents, the methyl carbonate of α,3,3-trimethyl cyclohexane methanol of our invention can be formulated into or used as a component of a "perfume composition".

The term "perfume composition" is used herein to mean a mixture of organic compounds including, for example, alcohols, aldehydes, ketones, nitriles, ethers, lactones, esters other than the carbonate of our invention, and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) top notes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of the methyl carbonate of α,3,3-trimethyl cyclohexane methanol of our invention having the structure:

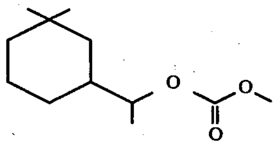

which will be effective in perfume compositions depends upon many factors including the other ingredients, their amounts and the effects which are desired. It has been found that perfume compositions containing as little as 0.1% of the methyl carbonate of α,3,3-trimethyl cyclohexane methanol of our invention or even less and perfume compositions containing as much as 70% of the methyl carbonate of α,3,3-trimethyl cyclohexane methanol of our invention can be used to impart interesting woody, floral (carnation), animalic (castoreum), spicy (cardamon), ylang, cananga and caryophyllene-like aromas to perfumed articles, perfume compositions and colognes. Such perfumed articles include fabric softener compositions, drier-added fabric softener articles, cosmetic powders, talcs, solid or liquid anionic, cationic, nonionic or zwitterionic detergents and perfumed polymers. The amount employed can range up to 70% and will depend on considerations of cost, nature of the end product and the effect desired on the finished product and particular fragrance sought.

Thus, the methyl carbonate of α,3,3-trimethyl cyclohexane methanol of our invention can be used alone or in a perfume composition as an olfactory component, in solid or liquid anionic, cationic, nonionic or zwitterionic detergents (including soaps), perfumed polymers (those which are microporous and those which are macroporous and those which contain particular absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer, a macroporous polymer, a polymer containing an absorbent filler or such as a solid or liquid cationic, anionic, nonionic or zwitterionic detergent or of a cosmetic powder, as little as 0.01% of the methyl carbonate of α,3,3-trimethyl cyclohexane methanol of our invention will suffice to provide an interesting woody, floral (carnation), animalic (castoreum), spicy (cardamon), ylang, cananga and caryophyllene-like aroma. Generally, no more than 0.8% of the methyl carbonate of α,3,3-trimethyl cyclohexane methanol of our invention is required. Thus, the range of the methyl carbonate of α,3,3-trimethyl cyclohexane methanol operable in perfumed articles of our invention is from about 0.01% up to about 0.8%.

In addition, the perfume composition of our invention can contain a vehicle or carrier for the methyl carbonate of α,3,3-trimethyl cyclohexane methanol of our invention alone or with other ingredients. The vehicle can be a liquid such as an alcohol such as ethanol, a glycol such as propylene glycol or the like. The carrier can be an absorbent solid such as gum (e.g., xanthan gum, guar gum or gum arabic) or components for encapsulating the solvent as by coacervation using gelatin or as by polymerization around a liquid center as by polymerizing a urea formaldehyde prepolymer around a liquid perfume center.

The methyl carbonate of α,3,3-trimethyl cyclohexane methanol of our invention is blended into polymers when forming a perfume polymer by means of extrusion using a single or double screw extruder or technique such as those set forth in U.S. Pat. No. 4,247,498 issued on Jan. 27, 1981 which discloses microporous polymers which are capable of containing volatile substances such as perfumes and the like and forms ranging from films to blocks in intricate shapes from synthetic thermoplastic polymers such as olefinic condensation or oxidation polymers. The specification of U.S. Pat. No. 4,247,498 is incorporated by reference herein. Other techniques of blending the methyl carbonate of α,3,3-trimethyl cyclohexane methanol of our invention with polymers are exemplified in U.S. Pat. No. 3,505,432 (the specification for which is incorporated by reference herein) which discloses a method for scenting a polyolefin with such materials as the methyl carbonate of α,3,3-trimethyl cyclohexane methanol of our invention which comprises:

(a) Mixing a first amount of a liquid polyolefin, e.g., polyethylene or polypropylene with a relatively large amount of scenting imparting material (in this case, methyl carbonate of α,3,3-trimethyl cyclohexane methanol) to form a flowable mass;

(b) forming drops of said mass and causing substantially instantaneous solidification of said drops into polyolefin pellets having a relatively large amount of such scent imparting materials as methyl carbonate of α,3,3-trimethyl cyclohexane methanol imprisoned therein;

(c) melting said pellets with the second amount of said polyolefin and said second amount being larger than said first amount; and (d) solidifying the melt of (c).

The following example sets forth the process for preparing the methyl carbonate of α,3,3-trimethyl cyclohexane methanol of our invention. The following Example II, et seq. represent methods for using the methyl carbonate of α,3,3-trimethyl cyclohexane methanol of our invention for its organoleptic properties.

Unless otherwise indicated, all parts and percentages are by weight.

EXAMPLE I

Preparation of Methyl Carbonate of α,3,3-Trimethyl Cyclohexane Methanol

Reaction:

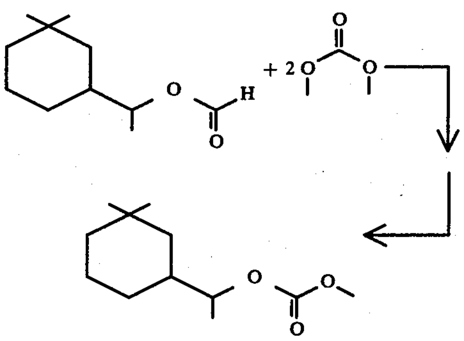

Into a 5-liter reaction vessel equipped with stirrer, thermometer and reflux condensor is placed 2,000 grams of dimethyl carbonate (23 moles) and 60 grams of sodium methoxide (1.1 mole) and 250 grams of the compound having the structure:

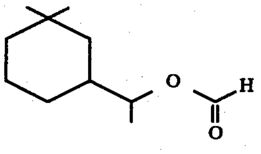

(α,3,3-trimethyl cyclohexyl methyl formate). The reaction mass is heated with stirring until methyl formate forms and is being distilled out. Over a period of 2 hours while maintaining the reaction mass at 67°-70° C., additional α,3,3-trimethyl cyclohexyl formate having the structure:

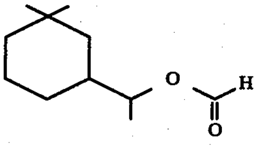

is added from an addition funnel into the reaction mass (total formate ester added: 2,500 grams . . . 13 moles). At the end of the addition the reaction mass is stirred at reflux for a period of 40 minutes. The reaction mass is then cooled to room temperature and 500 ml water is added with stirring. The acquiesce phase is separated from the organic phase and the organic phase is washed with one 500 ml volume of saturated acquiesce sodium chloride. The reaction mass is then evaporated on a rotary evaporator to distill off the lights and is then distilled to yield the following six fractions on a 2" splash column:

| Fraction No. | Vapor Temp. (°C.) | Liquid Temp. (°C.) | Vacuum mm/Hg. Pressure |
|---|---|---|---|
| 1 | 33/87 | 32/92 | 2.5/2.7 |
| 2 | 90 | 94 | 2.3 |
| 3 | 95 | 100 | 2.3 |
| 4 | 103 | 113 | 2.3 |

-continued

| Fraction No. | Vapor Temp. (°C.) | Liquid Temp. (°C.) | Vacuum mm/Hg. Pressure |
|---|---|---|---|
| 5 | 135 | 164 | 2.4 |
| 6 | 148 | 185 | 2.4 |

Fractions 3-5 from the 2" splash column distillation are then bulked and redistilled on a 1 foot Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 70/73 | 100/105 | 2.8/ | 4:1 | 88 |
| 2 | 75 | 105 | 2.6 | 4:1 | 82 |
| 3 | 75 | 107 | 2.6 | 4:1 | 78 |
| 4 | 79 | 108 | 2.6 | 4:1 | 77 |
| 5 | 91 | 105 | 2.6 | 4:1 | 92 |
| 6 | 92 | 106 | 2.6 | 4:1 | 119 |
| 7 | 92 | 106 | 2.6 | 4:1 | 96 |
| 8 | 92 | 106 | 2.6 | 4:1 | 114 |
| 9 | /92 | /106 | /2.6 | 4:1 | 35 |
| 10 | 93 | 108 | 2.6 | 4:1 | 88 |
| 11 | 93 | 108 | 2.6 | 4:1 | 91 |
| 12 | 93 | 108 | 2.6 | 4:1 | 87 |
| 13 | 93 | 108 | 2.6 | 4:1 | 90 |
| 14 | 93 | 108 | 2.6 | 1:1 | 96 |
| 15 | 93 | 110 | 2.6 | 1:1 | 354 |
| 16 | 93 | 130 | 2.6 | 1:1 | 97 |
| 17 | 93 | 170 | 2.6 | 1:1 | 48 |

Fractions 4-6 are bulked. These fractions have a woody, floral (carnation) animalic (castoreum), spicy (cardamon), ylang and caryophyllene-like aroma profile.

Figure 1:
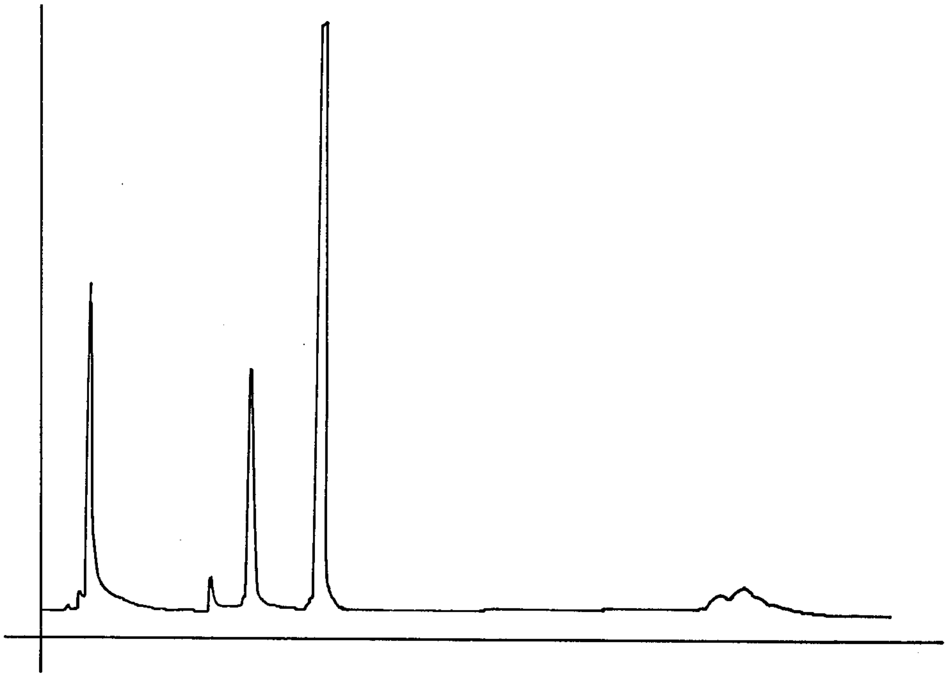
FIG. 1 is the GLC profile for the crude reaction product of Example 1 containing the compound having the structure.

FIG. 1 is the GLC profile of the crude reaction product prior to distillation.

FIG. 2 is the GLC profile for Fraction 5 of the foregoing distillation.

FIG. 3 is the NMR spectrum for the compound having the structure:

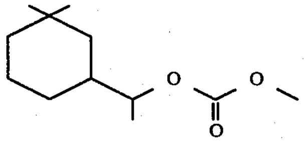

(Conditions: Field strength 100 MHz; solvent $CFCl_3$).

EXAMPLE II

Herbal Fragrance Formulation Produced Using the Product Prepared According to Example I The following mixture is prepared:

| Ingredients | Parts by Weight |
|---|---|
| Amyl cinnamic aldehyde | 20 |
| Phenyl acetaldehyde dimethyl acetal | 4 |
| Thyme oil white | 8 |
| Sauge sclaree French | 8 |
| Galbanum oil | 4 |
| Juniper berry oil | 10 |
| Methyl octin carbonate | 4 |
| Linalyl acetate | 2 |
| Dihydro methyl jasmonate | 10 |
| Methyl carbonate of α,3,3-trimethyl cyclohexane methanol having the structure: 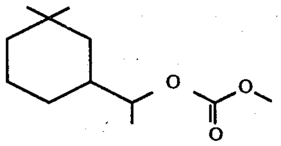 prepared according to Example I, bulked Fractions 4-6 | 10 |

The methyl carbonate of α,3,3-trimethyl cyclohexane methanol prepared according to Example I, adds to this herbal formulation a woody, floral (carnation), animalic (castoreum), spicy (cardamon), ylang, cananga and caryophyllene-like undertone to this herbal fragrance formulation causing it to be "tropical rain forest/patchouli-like/natural-like."

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Methyl carbonate of α,3,3-trimethyl cyclohexane methanol prepared according to Example I, bulked fractions 4-6 | A woody, floral (carnation), animalic (castoreum), spicy (cardamon), ylang, cananga and caryophyllene-like aroma. |
| Perfume composition of Example II. | An herbal aroma with woody, floral (carnation), animalic (castoreum), spicy (cardamon) ylang, cananga and caryophyllene-like undertones and a general "rain forest/patchoul natural-like" aroma. |

EXAMPLE IV

Perfumed Liquid Detergents

Concentrated liquid detergents (lysine salt of n-dodecylbenzene sulfonic acid as more specifically described in U.S. Pat. No. 3,948,818, issued on Apr. 6, 1976 incorporated by reference herein) with aroma nuances as set forth in Table I of Example III, are prepared containing 0.10%, 0.15%, 0.20%, 0.25%, 0.30% and 0.35% of the substance set forth in Table I of Example III. They are prepared by adding and homogeneously mixing the appropriate quantity of substance set forth in Table I of Example III in the liquid detergent. The detergents all possess excellent aromas as set forth in Table I of Example III, the intensity increasing with greater concentrations of substance as set forth in Table I of Example III.

EXAMPLE V

Preparation of Colognes and Handkerchief Perfumes

Compositions as set forth in Table I of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III are imparted to the colognes and to the handkerchief perfumes at all levels indicated.

EXAMPLE VI

Preparation of Soap Compositions

One hundred trams of soap chips (per sample) (IVORY ® produced by the Procter & Gamble Company of Cincinnati, Ohio), are each mixed with one gram samples of substances as set forth in Table I of Example III, until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS
   22% isopropyl alcohol
   20% antistatic agent
   1% of one of the substances as set forth in Table I of Example III.

Fabric softening compositions prepared according to Example I at column 15 of U.S. Pat. No. 3,632,396 having aroma characteristics as set forth in Table I of Example III supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example III, supra.

EXAMPLE IX

Hair Spray Formulations

The following hair spray formulation is prepared by first dissolving PVP/VA E-735 copolymer manufactured by the GAF Corporation of 140 West 51st St., New York, N.Y. in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example III | 0.10 weight percent |

The perfuming substances as set forth in Table I of Example III add aroma characteristics as set forth in Table I of Example III which are rather intense and aesthetically pleasing to the users of the soft-feel, good-hold pump hair sprays.

EXAMPLE X

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A."

Gafquat ®755 N polymer (manufactured by GAF Corporation of 140 West 51st St., New York, N.Y.) (5.0 weight percent) is admixed with 0.1 weight percent sodium sulfite and 1.4 weight percent polyethylene glycol 6000 distearate produced by Armak Corporation. This material is "Composition B."

The resulting "Composition A" and "Composition B" are then mixed in a 50:50 weight ratio of A:B and cooled to 45° C. and 0.3 weight percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

What is claimed is:

1. The methyl carbonate of α,3,3-trimethyl cyclohexane methanol having the structure:
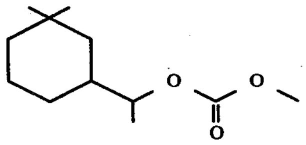
* * * * *